(12) United States Patent
Otsubo et al.

(10) Patent No.: US 11,427,763 B2
(45) Date of Patent: Aug. 30, 2022

(54) PYROLYSIS TUBE FOR MANUFACTURING OLEFIN AND METHOD FOR MANUFACTURING DEHYDROGENATING CATALYST

(71) Applicant: KUBOTA CORPORATION, Osaka (JP)

(72) Inventors: Kenji Otsubo, Osaka (JP); Kunihide Hashimoto, Osaka (JP); Hiroshi Yamaguchi, Osaka (JP); Yasushi Sekine, Tokyo (JP)

(73) Assignee: KUBOTA CORPORATION, Osaka (JP)

( * ) Notice: Subject to any disclaimer, the term of this patent is extended or adjusted under 35 U.S.C. 154(b) by 768 days.

(21) Appl. No.: 16/302,777

(22) PCT Filed: Apr. 4, 2017

(86) PCT No.: PCT/JP2017/014119
§ 371 (c)(1),
(2) Date: Nov. 19, 2018

(87) PCT Pub. No.: WO2017/199612
PCT Pub. Date: Nov. 23, 2017

(65) Prior Publication Data
US 2019/0309229 A1  Oct. 10, 2019

(30) Foreign Application Priority Data

May 20, 2016 (JP) .............................. JP2016-101731
Nov. 15, 2016 (JP) .............................. JP2016-222717

(51) Int. Cl.
*C10G 9/20* (2006.01)
*B01J 21/04* (2006.01)
(Continued)

(52) U.S. Cl.
CPC .............. *C10G 9/203* (2013.01); *B01J 21/04* (2013.01); *B01J 23/06* (2013.01); *B01J 23/08* (2013.01);
(Continued)

(58) Field of Classification Search
CPC . C10G 9/203; B01J 21/04; B01J 23/06; B01J 23/08; B01J 35/1014; B01J 37/0225; B01J 37/088; C07C 5/3332
See application file for complete search history.

(56) References Cited

U.S. PATENT DOCUMENTS 2,265,641 A   12/1941   Gorsskinsky et al.
3,960,767 A   6/1976    Christmann et al.
(Continued)

FOREIGN PATENT DOCUMENTS

| JP | 51-125007 A | 11/1976 |
|---|---|---|
| JP | 11-029776 | 2/1999 |
| JP | 2001-240401 A | 9/2001 |
| JP | 2005-120281 A | 5/2005 |
| JP | 2007-530260 A | 11/2007 |
| WO | 2010/113830 A1 | 10/2010 |

*Primary Examiner* — James A Fiorito
(74) *Attorney, Agent, or Firm* — McCarter & English, LLP; David G. Conlin

(57) ABSTRACT

The present invention provides a pyrolysis tube for manufacturing olefin which tube can improve a yield of olefin in a pyrolysis reaction of a hydrocarbon raw material. The pyrolysis tube (1A) for manufacturing olefin includes a tubular base material (2) made of a heat resistant metal material and a dehydrogenating catalyst (4A) which is supported on an inner surface of the tubular base material (2).

8 Claims, 7 Drawing Sheets

(51) Int. Cl.
*B01J 23/06* (2006.01)
*B01J 23/08* (2006.01)
*B01J 35/10* (2006.01)
*B01J 37/02* (2006.01)
*B01J 37/08* (2006.01)
*C07C 5/333* (2006.01)

(52) U.S. Cl.
CPC ....... *B01J 35/1014* (2013.01); *B01J 37/0225* (2013.01); *B01J 37/088* (2013.01); *C07C 5/3332* (2013.01); *C07C 2521/04* (2013.01); *C07C 2523/06* (2013.01); *C07C 2523/08* (2013.01); *C10G 2300/1044* (2013.01); *C10G 2300/70* (2013.01); *C10G 2400/20* (2013.01); *Y02P 20/52* (2015.11)

(56) References Cited

U.S. PATENT DOCUMENTS

| | | | | |
|---|---|---|---|---|
| 5,414,182 | A * | 5/1995 | Iezzi | B01J 37/18 |
| | | | | 585/661 |
| 2005/0272965 | A1* | 12/2005 | Watson | C01B 3/386 |
| | | | | 585/658 |
| 2011/0263416 | A1 | 10/2011 | Choi et al. | |
| 2011/0295051 | A1 | 12/2011 | Wang et al. | |
| 2011/0318593 | A1 | 12/2011 | Takahashi et al. | |

* cited by examiner (a)

(b)

(a)

(b)

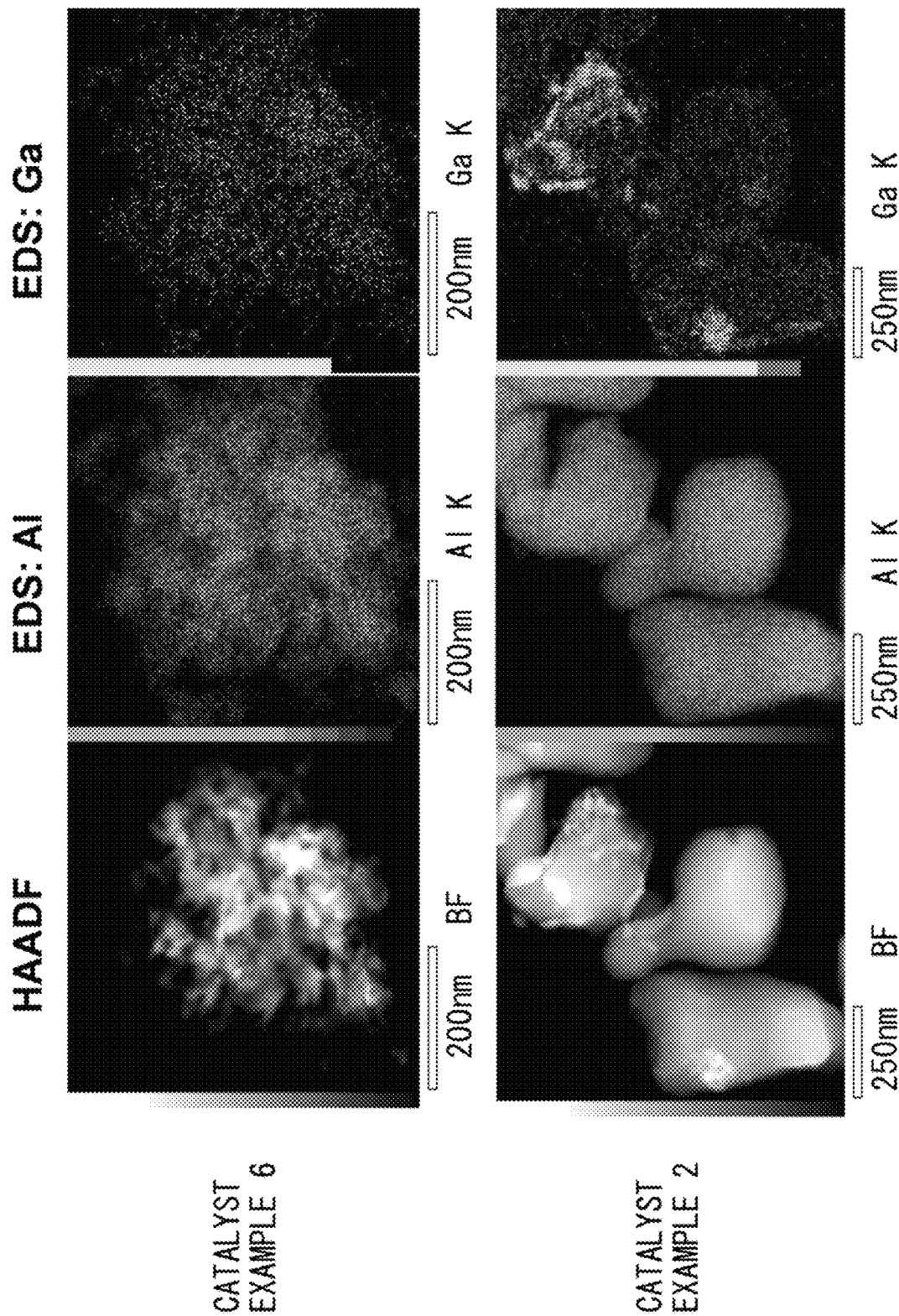

PYROLYSIS TUBE FOR MANUFACTURING OLEFIN AND METHOD FOR MANUFACTURING DEHYDROGENATING CATALYST

CROSS REFERENCE TO RELATED APPLICATION

The present application is a National Stage Entry of the International Patent Application No. PCT/JP2017/014119 filed Apr. 4, 2017, which also claims the benefit of priority of the Japanese Patent Application No. 2016-101731 filed May 20, 0216 and Japanese Patent Application No. 2016-222717 filed Nov. 15, 2016. The entire contents of those applications are incorporated herein for all purposes by this reference.

TECHNICAL FIELD

The present invention relates to a pyrolysis tube for manufacturing olefin with which tube a hydrocarbon raw material such as ethane or naphtha is pyrolyzed into olefin, and to a method for manufacturing a dehydrogenating catalyst which is supported on the pyrolysis tube for manufacturing olefin.

BACKGROUND ART

Olefin such as ethylene and propylene is used to manufacture chemical synthetic products for various purposes of use in industries. Olefin is manufactured by supplying petroleum-derived hydrocarbon such as ethane or naphtha into a pyrolysis tube (cracking tube), and pyrolyzing the hydrocarbon in a gas phase by heating at 700° C. to 900° C. In the manufacturing method, a large amount of energy is required to obtain a high temperature. Moreover, pyrolysis of hydrocarbon has various problems such as deposition of carbon (coke) on an inner surface of the pyrolysis tube and a carburization phenomenon that occurs on the inner surface of the pyrolysis tube. Under the circumstances, development of a high-performance pyrolysis tube that may solve those problems is demanded.

Patent Literature 1 and Patent Literature 2 disclose casting products which solve the above problems.

In the casting product disclosed in Patent Literature 1, a barrier layer containing $Al_2O_3$ is provided on an inner surface of a casting article which is made of heat resistant alloy. With the configuration, the casting product disclosed in Patent Literature 1 can prevent oxygen, carbon, nitrogen, and the like from intruding inside the casting article even in a case where the casting product is used in a high-temperature atmosphere.

In the casting product disclosed in Patent Literature 2, an inner surface is provided with a catalyst layer that is constituted by a perovskite catalyst which is in particular a perovskite catalyst containing elements such as barium (Ba), cerium (Ce), zirconium (Zr), or yttrium (Y) from which a basic oxide is formed. With the configuration, the casting product disclosed in Patent Literature 2 has an anti-coking function to decompose coke, which has been deposited on the inner surface, into hydrogen or carbonic acid gas by the catalyst layer, and can thus inhibit deposition of coke on the inner surface.

CITATION LIST

Patent Literature

[Patent Literature 1]
International Publication No. 2010/113830 (Publication date: Oct. 7, 2010) [Patent Literature 2]
US Patent Application Publication No. 2011/0295051 (Publication date: Dec. 1, 2011)

SUMMARY OF INVENTION

Technical Problem

According to the casting product disclosed in Patent Literature 1 or Patent Literature 2, a coating formed on the surface prevents oxygen, carbon, nitrogen, and the like from intruding inside the casting article, and this makes it possible to maintain excellent oxidation resistance, carburization resistance, nitridation resistance, corrosion resistance, and the like over a long period of time. However, development of a pyrolysis tube having higher performance is still demanded.

The present invention is accomplished in view of the problems, and its object is to provide a pyrolysis tube for manufacturing olefin which tube can improve a yield of olefin in a pyrolysis reaction of a hydrocarbon raw material.

Solution to Problem

In order to attain the object, a pyrolysis tube for manufacturing olefin in accordance with an aspect of the present invention is configured to include: a tubular base material made of a heat resistant metal material; and a dehydrogenating catalyst which is supported on an inner surface of the tubular base material.

In order to attain the object, a pyrolysis tube for manufacturing olefin in accordance with an aspect of the present invention is configured to include: a tubular base material made of a heat resistant metal material; a metal oxide coating which is provided on an inner surface of the tubular base material; and a dehydrogenating catalyst which is supported on a surface of the metal oxide coating.

Advantageous Effects of Invention

The present invention brings about an effect of providing the pyrolysis tube for manufacturing olefin which tube can improve a yield of olefin in a pyrolysis reaction of a hydrocarbon raw material.

BRIEF DESCRIPTION OF DRAWINGS

FIG. 7 is a view showing results of observation and measurement with use of TEM-EDS with respect to the dehydrogenating catalyst that is supported by the pyrolysis tube for manufacturing olefin in accordance with an aspect of the present invention. Specifically, FIG. 7 shows HAADF images and results of EDS mapping measurement carried out with respect to Al and Ga.

DESCRIPTION OF EMBODIMENTS

Embodiment 1

Figure 1:
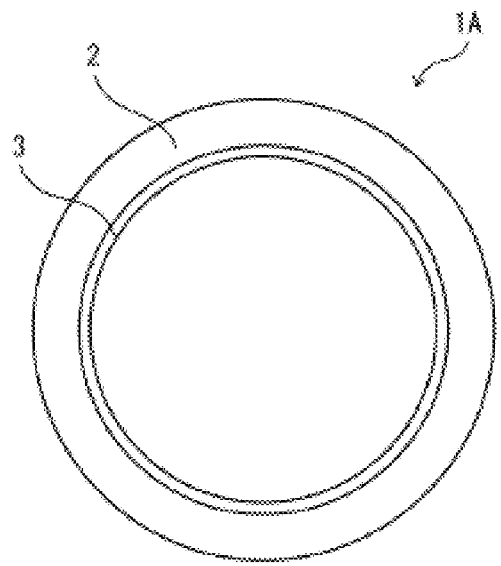
FIG. 1 is a view illustrating a configuration of a pyrolysis tube for manufacturing olefin in accordance with Embodiment 1 of the present invention, in which (a) of FIG. 1 is a cross-sectional view schematically illustrating the pyrolysis tube for manufacturing olefin, and (b) of FIG. 1 is an enlarged view illustrating an inner surface of the pyrolysis tube for manufacturing olefin illustrated in (a) of FIG. 1.
Figure 1:
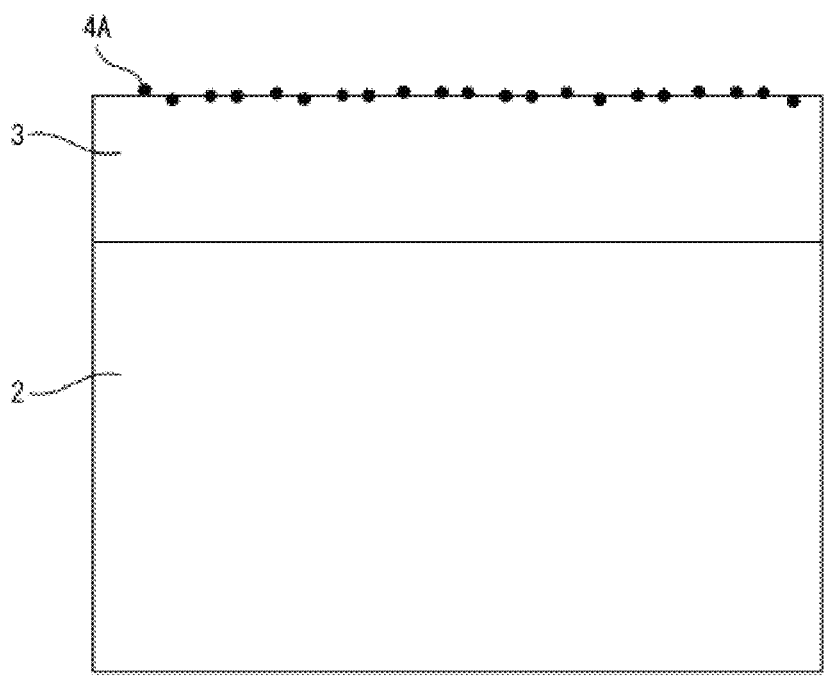

The following description will discuss details of a pyrolysis tube 1A for manufacturing olefin in accordance with Embodiment 1 of the present invention with reference to FIG. 1. FIG. 1 is a view illustrating a configuration of the pyrolysis tube 1A in accordance with Embodiment 1, in which (a) of FIG. 1 is a cross-sectional view schematically illustrating the pyrolysis tube 1A, and (b) of FIG. 1 is an enlarged view illustrating an inner surface of the pyrolysis tube 1A illustrated in (a) of FIG. 1.

As illustrated in (a) and (b) of FIG. 1, the pyrolysis tube 1A in accordance with Embodiment 1 includes a tubular base material 2 made of a heat resistant metal material, an alumina coating 3 which is a metal oxide coating containing $Al_2O_3$ and is provided on an inner surface of the tubular base material 2, and a dehydrogenating catalyst 4A which is supported on a surface of the alumina coating 3. In the present application, the metal oxide coating containing $Al_2O_3$ is referred to as "alumina coating". In a case where the pyrolysis tube 1A of an aspect of the present invention having this configuration is used in a pyrolysis reaction, a dehydrogenating catalyst reaction is added, and thus the pyrolysis tube 1A can improve a yield of olefin obtained from a hydrocarbon raw material such as ethane or naphtha. The following description will discuss details of the base material 2, the alumina coating 3, and the dehydrogenating catalyst 4A which are included in the pyrolysis tube 1A.

(Base Material 2)

The base material 2 in accordance with Embodiment 1 is a casting matter made of a heat resistant metal material, and the alumina coating 3 is provided on the surface of the base material 2. Note that the alumina coating 3 is more preferably α-$Al_2O_3$. The base material 2 at least contains, in mass %, chromium (Cr): 15% to 50%, nickel (Ni): 18% to 70%, and aluminum (Al): 1% to 6%. More preferably, the base material 2 contains carbon (C): 0.3% to 0.7%, silicon (Si): 0.1% to 1.5%, manganese (Mn): 0.1% to 3%, chromium (Cr): 15% to 40%, nickel (Ni): 18% to 55%, aluminum (Al): 2% to 4%, a rare-earth element: 0.005% to 0.4%, and tungsten (W): 0.5% to 5% and/or molybdenum (Mo): 0.1% to 3%, and the rest which is 25% or more and is iron (Fe), and inevitable impurities. Note that, unless otherwise noted, "%" in the whole specification represents "mass %".

<Reasons for Limiting Components of the Base Material 2>

(1) Carbon (C): 0.3% to 0.7%

Carbon (C) has functions to improve castability and enhance high temperature creep rupture strength. Therefore, at least 0.3% of carbon (C) is contained. However, in a case where a contained amount of carbon (C) is too large, primary carbide of $Cr_7C_3$ is more likely to be formed widely, and this restricts movement of aluminum (Al) which forms the alumina coating 3. This causes lack of aluminum (Al) which is to be supplied to a surface of the casting article, and hence the alumina coating 3 is locally broken, and thus continuity of the alumina coating 3 is impaired. Moreover, secondary carbide is excessively deposited, and this leads to deterioration in ductility and toughness. Therefore, an upper limit of the contained amount of carbon (C) is 0.7%. Note that the contained amount of carbon (C) is more preferably 0.4% to 0.6%.

(2) Silicon (Si): 0.1% to 1.5%

Silicon (Si) is contained in an amount of at least 0.1% as a deoxidant for a molten metal alloy and in order to heighten fluidity of the molten metal alloy. However, in a case where a contained amount of silicon (Si) is excessively large, high temperature creep rupture strength decreases, and therefore an upper limit of the contained amount of silicon (Si) is 1.5%. Note that the upper limit of the contained amount of silicon is more preferably 1.0%.

(3) Manganese (Mn): 0.1% to 3%

Manganese (Mn) is contained in an amount of at least 0.1% as a deoxidant for a molten metal alloy and in order to fix sulfur (S) in the molten metal. However, in a case where a contained amount of manganese (Mn) is excessively large, high temperature creep rupture strength decreases, and therefore an upper limit of the contained amount of manganese (Mn) is 3%. Note that the upper limit of the contained amount of manganese (Mn) is more preferably 1.0%.

(4) Chromium (Cr): 15% to 50%

Chromium (Cr) is contained in an amount of 15% or more for a purpose of contribution to improvement in high temperature strength and in repetitive oxidation resistance. However, in a case where a contained amount of chromium (Cr) is excessively large, high temperature creep rupture strength decreases, and therefore an upper limit of the contained amount of chromium (Cr) is 50%. Note that the contained amount of chromium (Cr) is more preferably 20% to 30%.

(5) Nickel (Ni): 18% to 70%

Nickel (Ni) is an element necessary for securing repetitive oxidation resistance and stability of metal structure, and is therefore contained in an amount of 18% or more. However, an upper limit of a contained amount of nickel (Ni) is 70% because an effect corresponding to an additional amount exceeding 70% cannot be brought about. Note that the contained amount of nickel (Ni) is more preferably 20% to 45%.

(6) Aluminum (Al): 1% to 6%

Aluminum (Al) is an element effective for improvement in carburization resistance and in coking resistance. Moreover, in the configuration recited in claim 2 of the present invention, aluminum (Al) is an element essential for forming the alumina coating 3 on the surface of the base material 2. Therefore, at least 1% or more of aluminum (Al) is contained. However, an upper limit of a contained amount of aluminum (Al) is specified to 6% in an aspect of the present invention because ductility decreases when the contained amount of aluminum (Al) exceeds 6%. Note that the contained amount of aluminum (Al) is more preferably 2% to 4%.

(7) Rare-Earth Element: 0.005% to 0.4%

The rare-earth elements indicate 17 elements including 15 elements of the lanthanum series from lanthanum (La) to lutetium (Lu) in the periodic table, yttrium (Y), and scandium (Sc).

The rare-earth element is contained in an amount of 0.005% or more because the rare-earth element has sulfur (S) fixation ability and oxide coating fixation ability which is achieved as a rare-earth oxide, and thus the rare-earth element contributes to facilitating generation and stability of the alumina coating 3. Meanwhile, ductility and toughness decrease in a case where the rare-earth element is excessively contained, and therefore an upper limit of a contained amount of the rare-earth element is 0.4%.

(8) Tungsten (W): 0.5% to 5% and/or Molybdenum (Mo): 0.1% to 3%

Each of tungsten (W) and molybdenum (Mo) reinforces an austenite phase of a base by being melted with the austenite phase in the base, and thus improves creep rupture strength. In order to bring about this effect, at least one of tungsten (W) (in an amount of 0.5% or more) and molybdenum (Mo) (in an amount of 0.1% or more) is contained.

However, in a case where contained amounts of tungsten (W) and molybdenum (Mo) are excessively large, ductility and carburization resistance decrease. Therefore, the contained amount of tungsten (W) is 5% or less, and the contained amount of molybdenum (Mo) is 3% or less. Note that the contained amount of tungsten (W) is more preferably 0.5% to 3%, and the contained amount of molybdenum (Mo) is more preferably 2% or less.

(9) At Least One of Titanium (Ti): 0.01% to 0.6%, Zirconium (Zr): 0.01% to 0.6%, and Niobium (Nb): 0.1% to 3.0%

Titanium (Ti), zirconium (Zr), and niobium (Nb) are elements that easily form carbides, and are less likely to be molten in a base as compared with tungsten (W) and molybdenum (Mo). Therefore, titanium (Ti), zirconium (Zr), and niobium (Nb) do not have particular effects on formation of the alumina coating 3 but can improve creep rupture strength. As needed, at least one of titanium (Ti), zirconium (Zr), and niobium (Nb) can be contained. A contained amount of titanium (Ti) is 0.01% or more, a contained amount of zirconium (Zr) is 0.01% or more, and a contained amount of niobium (Nb) is 0.1% or more.

However, in a case where titanium (Ti), zirconium (Zr), and niobium (Nb) are excessively added, ductility decreases. Therefore, an upper limit of the contained amount of titanium (Ti) is 0.6%, an upper limit of the contained amount of zirconium (Zr) is 0.6%, and an upper limit of the contained amount of niobium (Nb) is 3.0%. Note that the upper limit of the contained amount of titanium (Ti) is more preferably 0.3%, the upper limit of the contained amount of zirconium (Zr) is more preferably 0.3%, and the upper limit of the contained amount of niobium (Nb) is more preferably 1.5%.

(10) Boron (B): 0.1% or Less

Boron (B) has an effect of reinforcing a grain boundary of a casting article, and therefore can be contained as needed. Note that, in a case where a contained amount of boron (B) is excessively large, creep rupture strength decreases, and therefore an added amount of boron (B) is 0.1% or less.

(11) Iron (Fe): The Rest (25% or More)

With regard to a diffusion velocity of aluminum (Al) in iron (Fe), nickel (Ni), and chromium (Cr), the diffusion velocity seems to become higher as a size of atoms becomes smaller. Therefore, in a case where an amount of iron which is smaller in atom size is increased and an amount of chromium (Cr) is reduced, diffusion of aluminum (Al) in an alloy is enhanced and aluminum (Al) easily moves, and this makes it possible to facilitate formation of the alumina coating 3.

For the reasons above, iron (Fe) is contained in an amount of 25% or more. Note that the contained amount of iron (Fe) is more preferably 30% or more.

(12) Inevitable Impurities

Phosphorus (P), sulfur (S), and other impurities which are inevitably mixed in producing an alloy by melting metals can exist in the alloy, provided that an amount of such impurities falls within a range that is generally acceptable to that kind of alloy material.

<Method for Manufacturing Base Material 2>

The base material 2 in the pyrolysis tube 1A of an aspect of the present invention is manufactured by preparing a molten metal containing the above described components, and casting the molten metal with centrifugal casting, static casting, or the like such that the base material 2 has the early described composition.

The base material 2 thus obtained can have a shape corresponding to a purpose of use.

Note that the base material 2 of an aspect of the present invention is preferably prepared with centrifugal casting. This is because, in a case where the centrifugal casting is applied, fine metal structures grow with orientation in radial directions as a die is being cooled down, and this makes it possible to obtain an alloy structure in which aluminum (Al) easily moves. From this, in heat treatment which will be described later, it is possible to obtain a casting product in which the alumina coating 3 is provided which is thin and has excellent strength even in a repetitive heating environment.

The casting product produced by centrifugal casting can be, for example, a tube, in particular, a pyrolysis tube that is used in a high-temperature environment.

(Alumina Coating 3)

The alumina coating 3, which is provided on the inner surface of the base material 2 of an aspect of the present invention, has high denseness and serves as a barrier for preventing oxygen, carbon, and nitrogen from intruding into the base material 2 from outside.

In a general pyrolysis tube for manufacturing olefin, no metal oxide coating is provided on an inner surface of a base material 2. From this, a hydrocarbon raw material is excessively decomposed in pyrolysis due to an effect of catalysts such as nickel (Ni), iron (Fe), and cobalt (Co) which are constituent elements of the base material 2, and therefore coke is generated on the inner surface of the base material 2. In a case where coke generated on the inner surface of the base material 2 accumulates, heat transfer resistance is heightened. This causes the following problem: that is, in a case where a reaction temperature in the pyrolysis tube for manufacturing olefin is maintained, a temperature of an outer surface of the pyrolysis tube is raised. Moreover, in a case where coke accumulates on the inner surface of the base material 2, a cross-sectional area of a flow channel through which gas passes becomes smaller, and this leads to increase in pressure loss. For those reasons, in the general pyrolysis tube for manufacturing olefin, it has been necessary to frequently remove accumulated coke (i.e., decoking).

On the other hand, in the pyrolysis tube 1A of Embodiment 1, the alumina coating 3 is provided on the inner surface of the base material 2, and this makes it possible to restrict generation on coke on the inner surface. As a result, it is possible to reduce a frequency of carrying out decoking.

The alumina coating 3 of an aspect of the present invention is formed with a surface treatment step and a first heat treatment step. The following description will discuss details of the surface treatment step and the first heat treatment step.

<Surface Treatment Step>

The surface treatment step is a step of carrying out surface treatment with respect to a target site of the base material 2 which target site is to contact with a high temperature atmosphere when the product is used, and of adjusting surface roughness of the target site.

The surface treatment on the base material 2 can be, for example, polishing treatment. The surface treatment can be carried out such that the surface roughness (Ra) of the target site becomes 0.05 µm to 2.5 µm. More preferably, the surface roughness (Ra) is 0.5 µm to 2.0 µm. Moreover, by adjusting the surface roughness in the surface treatment, it is possible to concurrently remove residual stress and distortion of a heat affected zone.

<First Heat Treatment Step>

The first heat treatment step is a step of applying heat treatment to the base material 2 in an oxidizing atmosphere after the surface treatment step.

The oxidizing atmosphere indicates an oxidizing gas containing oxygen in an amount of 20 volume % or more or an oxidizing environment in which steam and $CO_2$ are mixed. The heat treatment is carried out at a temperature of 900° C. or higher, preferably 1000° C. or higher, and a heating time is 1 hour or longer.

By sequentially carrying out the surface treatment step and the first heat treatment step with respect to the base material 2, it is possible to obtain the pyrolysis tube for manufacturing olefin in which the alumina coating 3 is stably provided on the inner surface of the base material 2.

A thickness of the alumina coating 3 which is provided on the inner surface of the base material 2 is suitably 0.5 µm or more and 6 µm or less in order to effectively achieve a barrier function. In a case where the thickness of the alumina coating 3 is less than 0.5 µm, carburization resistance may decrease. In a case where the thickness of the alumina coating 3 is more than 6 µm, the alumina coating 3 may easily peel off due to influence of a difference in thermal expansion coefficient between the base material 2 and the coating.

In order to avoid such an influence, the thickness of the alumina coating 3 is more suitably 0.5 µm or more and 2.5 µm or less.

Note that, in a case where a surface of the pyrolysis tube 1A of an aspect of the present invention is investigated with SEM/EDX, chromium oxide scales are sometimes partially formed on the alumina coating 3. This is because chromium oxide scales formed in the vicinity of the surface of the base material 2 are forced up to a surface of the product by $Al_2O_3$. It is preferable that the chromium oxide scales less appear, and therefore an area of chromium oxide scales suitably accounts for 20% or less of the entire surface of the product such that an area of the $Al_2O_3$ accounts for 80% or more of the entire surface of the product.

(Dehydrogenating Catalyst 4A)

The dehydrogenating catalyst 4A is a catalyst for improving a yield of olefin in a pyrolysis reaction (specifically, a reaction to pyrolyze a hydrocarbon raw material such as naphtha or ethane into olefin) with use of the pyrolysis tube 1A. The dehydrogenating catalyst 4A is supported on a surface of the alumina coating 3.

The dehydrogenating catalyst 4A is constituted only by catalyst components which contain at least one selected from the group consisting of oxides of metallic elements in the group 2B of the periodic table, oxides of metallic elements in the group 3B of the periodic table, and oxides of metallic elements in the group 4B of the periodic table. More preferably, the dehydrogenating catalyst 4A is constituted only by catalyst components which contain at least one selected from the group consisting of Zn oxide (ZnO), Ga oxide ($Ga_2O_3$), Sn oxide (SnO or $SnO_2$), Ge oxide ($GeO_2$), and In oxide ($In_2O_3$).

Patent Literature 2 discloses a perovskite catalyst, in particular, a perovskite catalyst containing elements such as barium (Ba), cerium (Ce), zirconium (Zr), and yttrium (Y) from which a basic oxide is formed. Note, however, that the inventors of the present invention have found as a result of diligent study that oxides of metallic elements in the group 2B, oxides of metallic elements in the group 3B, and oxides of metallic elements in the group 4B, more preferably oxides of zinc (Zn), gallium (Ga), tin (Sn), germanium (Ge), and indium (In), which are not basic oxides but are acidic oxides, are effective as a catalyst for generating olefin by pyrolysis of hydrocarbon such as ethane or naphtha. Note that use of oxides of iron (Fe), cobalt (Co), nickel (Ni), and the like as catalysts is not preferable because the hydrocarbon raw material is excessively decomposed in pyrolysis, and a large amount of coke (carbon) may be generated on the surface of the alumina coating.

<Method for Forming Dehydrogenating Catalyst 4A and Causing Dehydrogenating Catalyst 4A to be Supported>

The following description will discuss a method for forming the dehydrogenating catalyst 4A, and a method for causing the dehydrogenating catalyst 4A to be supported on the alumina coating 3. The method for forming the dehydrogenating catalyst 4A and the method for causing the dehydrogenating catalyst 4A to be supported on the alumina coating 3 include an applying step and a second heat treatment step. The following description will discuss details of the applying step and the second heat treatment step.

(a) Applying Step

The applying step is a step of applying a metal salt aqueous solution, which contains metallic elements constituting the dehydrogenating catalyst 4A, to the surface of the alumina coating 3 which has been formed in the surface treatment step and the first heat treatment step.

The metal salt can be, for example, nitrate, acetate, and the like.

(b) Second Heat Treatment Step

The second heat treatment step is a step of heating the base material 2 in which the metal salt aqueous solution has been applied to the alumina coating 3 in the applying step.

The heat treatment in the second heat treatment step is carried out in the atmosphere or in oxygen. A heat treatment temperature in the second heat treatment step falls within a range from 500° C. to 900° C., and a heat treatment time is 1 hour to 6 hours.

By carrying out the second heat treatment step under the above described heat treatment conditions, metal ions in the metal salt are oxidized, and thus a metal oxide, that is, the dehydrogenating catalyst 4A is formed. As a result, the dehydrogenating catalyst 4A can be supported on the alumina coating 3.

Note that the dehydrogenating catalyst 4A can be supported on the alumina coating 3 at an appropriate concentration (amount) by adjusting a concentration of the metal salt aqueous solution that is applied in the applying step. Moreover, in order to improve catalytic ability of the dehydrogenating catalyst 4A in pyrolysis, a specific surface area of the dehydrogenating catalyst 4A is preferably 2 m$^2$/g to 100 m$^2$/g, more preferably 3 m$^2$/g to 10 m$^2$/g.

As such, the pyrolysis tube 1A in accordance with Embodiment 1 includes the tubular base material 2 made of the heat resistant metal material, the alumina coating 3 which is provided on the inner surface of the tubular base material 2, and the dehydrogenating catalyst 4A which is supported on the surface of the alumina coating 3.

According to the configuration, in the pyrolysis tube 1A of an aspect of the present invention, the alumina coating 3 is provided on the inner surface of the base material 2. This makes it possible to restrict generation of coke on the surface of the alumina coating 3 (base material 2). Further, the dehydrogenating catalyst 4A is supported on the surface of the alumina coating 3. With the configuration, in a case where the dehydrogenating catalyst 4A functions as a dehydrogenating catalyst in pyrolysis carried out with use of the pyrolysis tube 1A, for example, it is possible to generate ethylene from ethane by dehydrogenation. As a result, it is possible to improve a yield of olefin obtained from pyrolysis of a hydrocarbon raw material such as ethane or naphtha.

In Embodiment 1, the dehydrogenating catalyst 4A is constituted only by catalyst components which contain at least one selected from the group consisting of oxides of metallic elements in the group 2B of the periodic table, oxides of metallic elements in the group 3B of the periodic table, and oxides of metallic elements in the group 4B of the periodic table. More preferably, the dehydrogenating catalyst 4A is constituted only by catalyst components which contain at least one selected from the group consisting of Zn oxide (ZnO), Ga oxide (Ga$_2$O$_3$), Sn oxide (SnO or SnO$_2$), Ge oxide (GeO$_2$), and In oxide (In$_2$O$_3$). Those metal oxides function as dehydrogenating catalysts in pyrolysis for manufacturing olefin from a hydrocarbon raw material such as ethane or naphtha, and it is therefore possible to improve a yield of olefin such as ethylene.

In Embodiment 1, the metal salt aqueous solution containing metallic elements constituting the dehydrogenating catalyst 4A is applied to the alumina coating 3 in the applying step, and the dehydrogenating catalyst 4A is supported on the alumina coating 3 by carrying out heat treatment in the second heat treatment step. Note, however, that the pyrolysis tube for manufacturing olefin in the present invention is not limited to this. For example, it is possible to employ the following configuration: that is, the dehydrogenating catalyst 4A is prepared in advance, a slurry containing the dehydrogenating catalyst 4A is applied to the alumina coating 3 in the applying step, and the dehydrogenating catalyst 4A is supported on the alumina coating 3 by carrying out heat treatment in the second heat treatment step with respect to the base material 2 to which the slurry containing the dehydrogenating catalyst 4A has been applied. Note that, in this case, the dehydrogenating catalyst 4A is prepared in advance with any of publicly known methods.

Moreover, in Embodiment 1, the dehydrogenating catalyst 4A is supported on the alumina coating 3 by carrying out the applying step and the second heat treatment step with respect to the alumina coating 3 which has been provided on the inner surface of the base material 2 by the surface treatment step and the first heat treatment step. Note, however, that the pyrolysis tube for manufacturing olefin of the present invention is not limited to this. For example, it is possible that the applying step and the heat treatment step are carried out after the surface treatment step. In this case, in the heat treatment step, the alumina coating 3 is formed on the inner surface of the base material 2 and also the dehydrogenating catalyst 4A is supported on the alumina coating 3. From this, it is possible to form the alumina coating 3 on the inner surface of the base material 2 and also to cause the dehydrogenating catalyst 4A to be supported on the alumina coating 3 by carrying out the heat treatment step only once.

In Embodiment 1, the configuration is employed in which the dehydrogenating catalyst 4A is supported on the surface of the alumina coating 3 which is provided on the inner surface of the base material 2. Note, however, that the pyrolysis tube 1A of the present invention is not limited to this. That is, the pyrolysis tube for manufacturing olefin in accordance with an aspect of the present invention can employ a configuration in which the dehydrogenating catalyst 4A is supported on a surface of a metal oxide coating (e.g., Cr$_2$O$_3$, MnCr$_2$O$_4$, or the like) which is not Al$_2$O$_3$ but has a barrier function and can support the dehydrogenating catalyst 4A.

Modification Example

Figure 2:
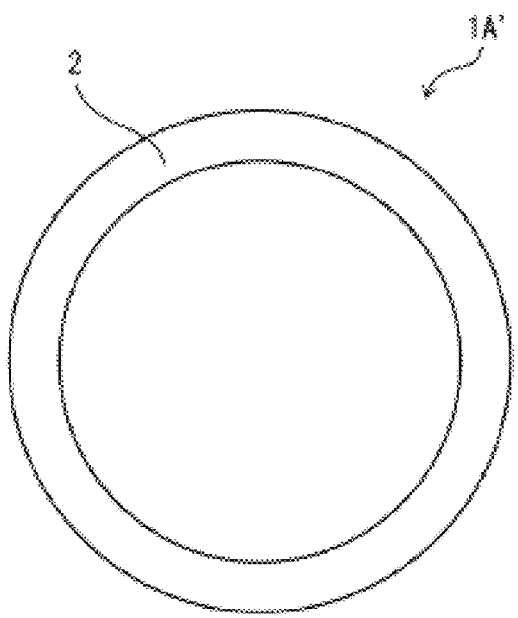
FIG. 2 is a view illustrating a configuration of a pyrolysis tube for manufacturing olefin which is a modification example of the above pyrolysis tube for manufacturing olefin, in which (a) of FIG. 2 is a cross-sectional view schematically illustrating the pyrolysis tube for manufacturing olefin, and (b) of FIG. 1 is an enlarged view illustrating an inner surface of the pyrolysis tube for manufacturing olefin illustrated in (a) of FIG. 2.
Figure 2:
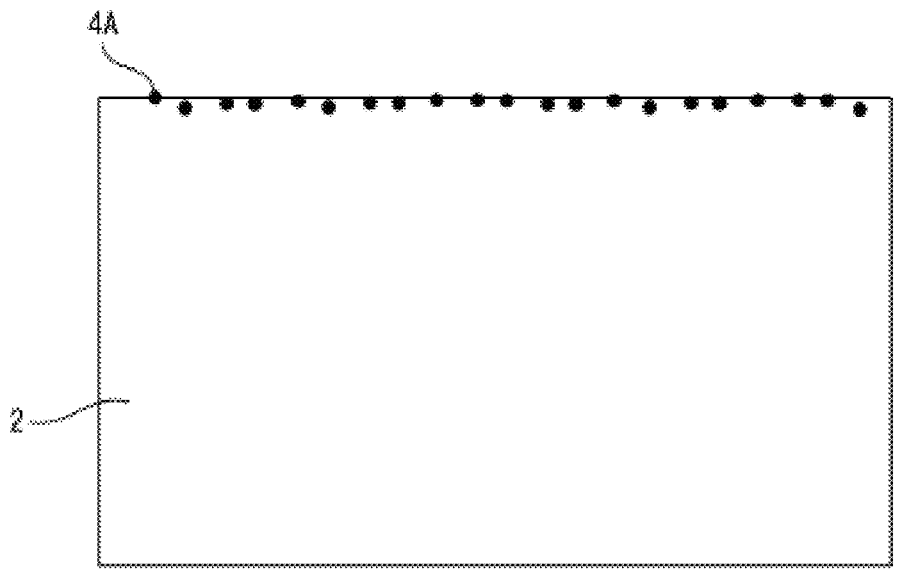

The following description will discuss a pyrolysis tube 1A', which is a modification example of the pyrolysis tube 1A in Embodiment 1, with reference to FIG. 2. FIG. 2 is a view illustrating a configuration of the pyrolysis tube 1A', in which (a) of FIG. 2 is a cross-sectional view schematically illustrating the pyrolysis tube 1A', and (b) of FIG. 2 is an enlarged view illustrating an inner surface of the pyrolysis tube 1A' illustrated in (a) of FIG. 2.

In the pyrolysis tube 1A in accordance with Embodiment 1, the alumina coating 3 which is a metal oxide coating containing Al$_2$O$_3$ is provided on the inner surface of the base material 2, and the dehydrogenating catalyst 4A is supported on the surface of the alumina coating 3. The pyrolysis tube 1A' which is a modification example is different from the pyrolysis tube 1A in that the dehydrogenating catalyst 4A is directly supported on the inner surface of the tubular base material 2 which is made of a heat resistant metal material (see (a) and (b) of FIG. 2).

In the pyrolysis tube 1A' of this modification example, a metal salt aqueous solution which contains metallic elements constituting the dehydrogenating catalyst 4A or a slurry which contains the dehydrogenating catalyst 4A prepared in advance is applied to the inner surface of the base material 2, and heat treatment is carried out under appropriate conditions such as in the atmosphere or in a nitrogen atmosphere. From this, the dehydrogenating catalyst 4A can be supported on the inner surface of the base material 2.

As above described, in the pyrolysis tube 1A', the dehydrogenating catalyst 4A is supported on the inner surface of the base material 2. With the configuration, in a case where the dehydrogenating catalyst 4A functions as a dehydrogenating catalyst in pyrolysis carried out with use of the pyrolysis tube 1A', for example, it is possible to generate ethylene from ethane by dehydrogenation. As a result, it is possible to improve a yield of olefin obtained from pyrolysis of a hydrocarbon raw material such as ethane or naphtha.

Embodiment 2

Figure 3:
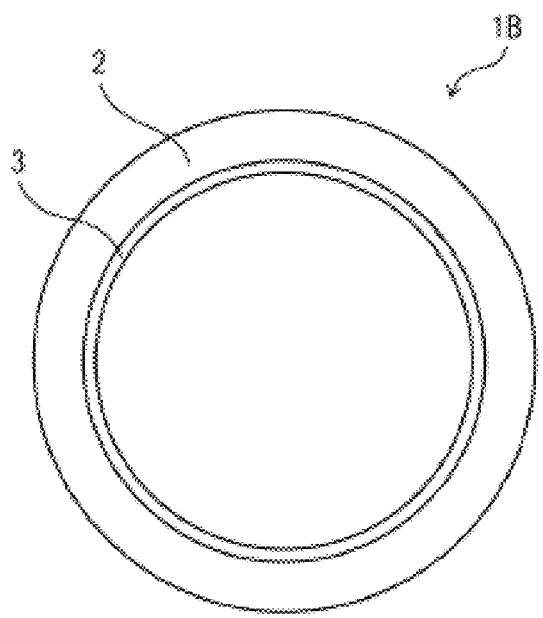
FIG. 3 is a view illustrating a configuration of a pyrolysis tube for manufacturing olefin in accordance with Embodiment 2 of the present invention, in which (a) of FIG. 3 is a cross-sectional view schematically illustrating the pyrolysis tube for manufacturing olefin, and (b) of FIG. 3 is an enlarged view illustrating an inner surface of the pyrolysis tube for manufacturing olefin illustrated in (a) of FIG. 3.
Figure 3:
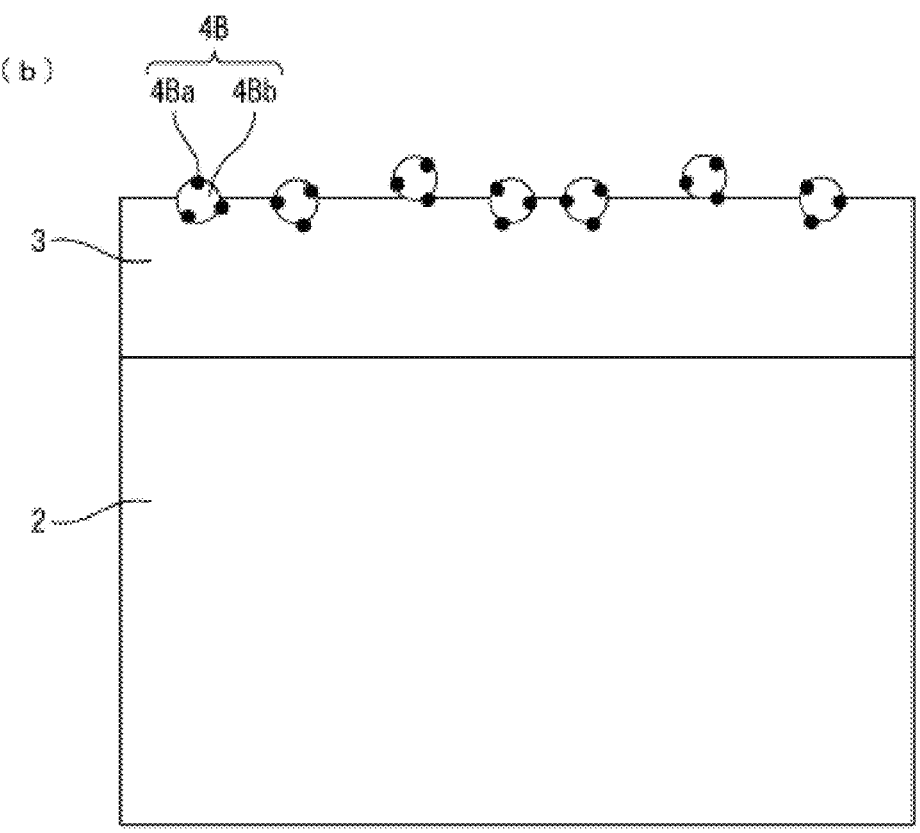

The following description will discuss another embodiment of the present invention with reference to FIG. 3. For convenience of explanation, the same reference numerals are given to constituent members which have functions identical with those described in Embodiment 1, and descriptions regarding such constituent members are omitted.

In a pyrolysis tube 1B for manufacturing olefin in accordance with Embodiment 2, a dehydrogenating catalyst has a configuration different from that of the dehydrogenating catalyst 4A in Embodiment 1.

(Dehydrogenating Catalyst 4B)

The following description will discuss details of the pyrolysis tube 1B in accordance with Embodiment 2 of the present invention with reference to FIG. 3. FIG. 3 is a view illustrating a configuration of the pyrolysis tube 1B in accordance with Embodiment 2, in which (a) of FIG. 3 is a cross-sectional view schematically illustrating the pyrolysis tube 1B, and (b) of FIG. 3 is an enlarged view illustrating an inner surface of the pyrolysis tube 1B illustrated in (a) of FIG. 3.

A dehydrogenating catalyst 4B in the pyrolysis tube 1B of Embodiment 2 contains a catalyst component 4Ba and a carrier 4Bb for supporting the catalyst component (see (a) and (b) of FIG. 3).

The catalyst component 4Ba is a catalyst component in the dehydrogenating catalyst 4B for improving a yield of olefin in a pyrolysis reaction by which a hydrocarbon raw material such as ethane or naphtha is pyrolyzed into olefin. The catalyst component 4Ba contains at least one selected from the group consisting of oxides of metallic elements in the group 2B of the periodic table, oxides of metallic elements in the group 3B of the periodic table, and oxides of metallic elements in the group 4B of the periodic table. More preferably, the catalyst component 4Ba contains at least one selected from the group consisting of Zn oxide (ZnO), Ga oxide ($Ga_2O_3$), Sn oxide (SnO or $SnO_2$), Ge oxide ($GeO_2$), and In oxide ($In_2O_3$).

The carrier 4Bb is a carrier for supporting the catalyst component 4Ba in the dehydrogenating catalyst 4B. The carrier 4Bb in accordance with Embodiment 2 is constituted by $Al_2O_3$. The carrier 4Bb preferably has a large specific surface area in order to improve a catalytic function of the catalyst component 4Ba. Specifically, the specific surface area of $Al_2O_3$ serving as the carrier 4Bb is preferably 20 $m^2/g$ or more, more preferably 40 $m^2/g$ or more. With the configuration, it is possible to highly disperse the catalyst component 4Ba in the carrier 4Bb. As a result, it is possible to improve a yield of olefin in a pyrolysis reaction by which a hydrocarbon raw material is pyrolyzed into olefin. Note that $Al_2O_3$ has the following four phases: that is, $\gamma$-$Al_2O_3$, $\delta$-$Al_2O_3$, $\theta$-$Al_2O_3$, and $\alpha$-$Al_2O_3$. For example, in a case where $\gamma$-$Al_2O_3$ is subjected to heat treatment, phase transformation occurs in the following order: ($\gamma$-$Al_2O_3$)→($\delta$-$Al_2O_3$)→($\theta$-$Al_2O_3$)→($\alpha$-$Al_2O_3$) as a heat treatment temperature rises. As the phase transformation proceeds, a specific surface area becomes smaller. In particular, $\alpha$-$Al_2O_3$ whose phase is transformed at a highest temperature has a specific surface area of 15 $m^2/g$ or less. Therefore, the carrier 4Bb of the dehydrogenating catalyst 4B in accordance with Embodiment 2 preferably has the specific surface area of 20 $m^2/g$ or more as above described. This means that it is preferable that the carrier 4Bb has a configuration mainly containing $\gamma$-$Al_2O_3$, $\delta$-$Al_2O_3$, or $\theta$-$Al_2O_3$.

Note that, in a case where $\gamma$-$Al_2O_3$ is used as a starting material of the carrier 4Bb, the phase of $\gamma$-$Al_2O_3$ is gradually transformed by heat treatment, and therefore $Al_2O_3$ serving as the carrier 4Bb does not have a single phase except before the heat treatment and after the heat treatment at a high temperature of 1300° C. or higher. That is, $\gamma$-$Al_2O_3$, $\delta$-$Al_2O_3$, $\theta$-$Al_2O_3$, and $\alpha$-$Al_2O_3$ would exist in a mixed manner. For this reason, the specific surface area of $Al_2O_3$ serving as the carrier 4Bb is an average of specific surface areas of the mixed phases of $Al_2O_3$.

The carrier 4Bb preferably forms a composite oxide or a solid solution with the catalyst component 4Ba in manufacture of the dehydrogenating catalyst 4B. From this, it is possible to inhibit aggregation of the catalyst component 4Ba in the pyrolysis reaction for pyrolyzing the hydrocarbon raw material into olefin. Consequently, it is possible to maintain a state in which a yield of olefin is high for a long time, and this makes it possible to further improve the yield of olefin. Specifically, it is preferable that at least part of the carrier 4Bb is $\theta$-$Al_2O_3$.

<Method for Manufacturing Dehydrogenating Catalyst 4B>

The following description will discuss a method for manufacturing the dehydrogenating catalyst 4B. In the descriptions below, two cases of the method for manufacturing the dehydrogenating catalyst 4B will be discussed, that is, (1) a case where $\alpha$-$Al_2O_3$ is used as a starting material of the carrier 4Bb and (2) a case where $\gamma$-$Al_2O_3$ is used as a starting material of the carrier 4Bb are described.

(1) Case where $\alpha$-$Al_2O_3$ is Used as a Starting Material of the Carrier 4Bb The dehydrogenating catalyst 4B can be manufactured by causing a metal salt (e.g., nitrate, acetate, or the like) aqueous solution which contains metallic elements constituting the catalyst component 4Ba to adhere to $\alpha$-$Al_2O_3$ used as a starting material of the carrier 4Bb, and then carrying out heat treatment. The heat treatment is carried out in the atmosphere or in oxygen, a heat treatment temperature falls within a range from 500° C. to 1300° C., and a heat treatment time is 1 hour to 6 hours. By carrying out the heat treatment under the above conditions, it is possible to obtain the dehydrogenating catalyst 4B in which the catalyst component 4Ba is supported by $\alpha$-$Al_2O_3$ serving as the carrier 4Bb.

(2) Case where $\gamma$-$Al_2O_3$ is Used as a Starting Material of Carrier 4Bb

The dehydrogenating catalyst 4B can be manufactured by causing a metal salt (e.g., nitrate, acetate, or the like) aqueous solution which contains metallic elements constituting the catalyst component 4Ba to adhere to $\gamma$-$Al_2O_3$ used as a starting material of the carrier 4Bb (adhering step), and then carrying out heat treatment (heat treatment step) with respect to $\gamma$-$Al_2O_3$ to which the metal salt aqueous solution has adhered. The heat treatment is carried out in the atmosphere or in oxygen, a heat treatment temperature falls within a range from 500° C. to 1300° C., and a heat treatment time is 1 hour to 6 hours. By carrying out the heat treatment under the above conditions, it is possible to obtain the dehydrogenating catalyst 4B in which the catalyst component 4Ba is supported by $Al_2O_3$ ($\gamma$-$Al_2O_3$, $\delta$-$Al_2O_3$, $\theta$-$Al_2O_3$, or $\alpha$-$Al_2O_3$) which serves as the carrier 4Bb.

Note that the heat treatment temperature preferably falls within a range from 500° C. to 1100° C. This is because, in a case where the heat treatment temperature falls within the range from 500° C. to 1100° C., it is possible to inhibit $\gamma$-$Al_2O_3$ from being completely phase-transformed into $\alpha$-$Al_2O_3$ during the heat treatment, and this makes it possible to inhibit decrease in specific surface area of $Al_2O_3$ serving as a carrier. As a result, it is possible to highly disperse the catalyst component 4Ba in $Al_2O_3$ serving as a carrier.

The heat treatment temperature more preferably falls within a range from 1000° C. to 1100° C. This is because, in a case where the heat treatment temperature falls within 1000° C. to 1100° C., at least part of γ-$Al_2O_3$ is phase-transformed into θ-$Al_2O_3$ during heat treatment, at least part of $Al_2O_3$ is coupled with the catalyst component 4Ba (in particular, gallium oxide) in the phase transformation, and thus a composite oxide or a solid solution is formed. From this, it is possible to inhibit aggregation of the catalyst component 4Ba in the pyrolysis reaction for pyrolyzing the hydrocarbon raw material into olefin.

The heat treatment temperature more preferably falls within a range from 1000° C. to 1080° C. This is because, in a case where the heat treatment temperature falls within the range from 1000° C. to 1080° C., it is possible to increase a ratio of phase transformation of γ-$Al_2O_3$ into θ-$Al_2O_3$ during the heat treatment.

<Method for Causing Dehydrogenating Catalyst 4B to be Supported>

The following description will discuss a method for causing the dehydrogenating catalyst 4B to be supported on the alumina coating 3. The method for causing the dehydrogenating catalyst 4B to be supported on the alumina coating 3 includes an applying step and a third heat treatment step. The following description will discuss details of the applying step and the third heat treatment step.

(a) Applying Step

The applying step is a step of applying a slurry containing the dehydrogenating catalyst 4B to a surface of the alumina coating 3 which has been formed by the surface treatment step and the first heat treatment step which are described in Embodiment 1.

(b) Third Heat Treatment Step

The third heat treatment step is a step of heating the base material 2 in which the slurry containing the dehydrogenating catalyst 4B has been applied to the alumina coating 3 in the applying step.

The heat treatment in the third heat treatment step is carried out in the atmosphere or in oxygen. A heat treatment temperature in the third heat treatment step falls within a range from 500° C. to 900° C., and a heat treatment time is 1 hour to 6 hours.

By carrying out the third heat treatment step under the above heat treatment conditions, it is possible to cause the dehydrogenating catalyst 4B to be supported on the alumina coating 3.

Next, characteristics of the dehydrogenating catalyst 4B supported on the alumina coating 3 are described.

Note that the dehydrogenating catalyst 4B can be supported on the alumina coating 3 at an appropriate concentration (amount) by adjusting a concentration of the slurry that is applied in the applying step. Moreover, in order to improve catalytic ability of the dehydrogenating catalyst 4B in pyrolysis, a specific surface area of the dehydrogenating catalyst 4B is preferably 2 $m^2/g$ to 200 $m^2/g$, more preferably 10 $m^2/g$ to 150 $m^2/g$, further preferably 20 $m^2/g$ to 100 $m^2/g$. Further, $Al_2O_3$ serving as the carrier 4Bb is mostly θ-$Al_2O_3$, and therefore a specific surface area of the dehydrogenating catalyst 4B is most preferably 40 $m^2/g$ to 100 $m^2/g$.

As such, the pyrolysis tube 1B in accordance with Embodiment 2 includes the tubular base material 2 made of the heat resistant metal material, the alumina coating 3 which is provided on the inner surface of the tubular base material 2, and the dehydrogenating catalyst 4B which is supported on the surface of the alumina coating 3. The dehydrogenating catalyst 4B contains the catalyst component 4Ba and the carrier 4Bb for supporting the catalyst component 4Ba. The catalyst component 4Ba contains at least one selected from the group consisting of oxides of metallic elements in the group 2B of the periodic table, oxides of metallic elements in the group 3B of the periodic table, and oxides of metallic elements in the group 4B of the periodic table. More preferably, the catalyst component 4Ba contains at least one selected from the group consisting of Zn oxide (ZnO), Ga oxide ($Ga_2O_3$), Sn oxide (SnO or $SnO_2$), Ge oxide ($GeO_2$), and In oxide ($In_2O_3$). The carrier 4Bb is constituted by $Al_2O_3$, more preferably at least part of the carrier 4Bb is constituted by θ-$Al_2O_3$.

According to the configuration, in the pyrolysis tube 1B of an aspect of the present invention, the dehydrogenating catalyst 4B in which the carrier 4Bb supports the catalyst component 4Ba is supported on the surface of the alumina coating 3, and this makes it possible to enlarge a surface area of the alumina coating 3. As a result, dehydrogenating catalyst reaction locations of hydrocarbon can be increased in addition to the pyrolysis reaction of hydrocarbon, and this makes it possible to improve a yield of olefin obtained from the hydrocarbon raw material such as ethane or naphtha.

In the pyrolysis tube 1B in accordance with Embodiment 2, the carrier 4Bb for supporting the dehydrogenating catalyst is constituted by $Al_2O_3$. Note, however, that the pyrolysis tube for manufacturing olefin in accordance with the present invention is not limited to this, and it is possible to use, as the carrier, $SiO_2$, $TiO_2$, $ZrO_2$, MgO, $La_2O_3$, or a composite oxide containing those. Note that, in view of surface area, it is more preferable to use $Al_2O_3$.

Moreover, in Embodiment 2, the dehydrogenating catalyst 4B is supported on the alumina coating 3 by carrying out the applying step and the third heat treatment step with respect to the alumina coating 3 which has been provided on the inner surface of the base material 2 by the surface treatment step and the first heat treatment step. Note, however, that the pyrolysis tube for manufacturing olefin of the present invention is not limited to this. For example, it is possible to employ a configuration in which $Al_2O_3$, to which a metal salt aqueous solution containing metallic elements constituting the catalyst component 4Ba has adhered, is applied to the inner surface of the base material 2 after the surface treatment step, and then the heat treatment step is carried out. In this case, in the heat treatment step, the alumina coating 3 is formed on the inner surface of the base material 2 and also the dehydrogenating catalyst 4B, in which the metal oxide is supported by $Al_2O_3$ by oxidation of metal in the metal salt, is supported on the alumina coating 3. From this, it is possible to form the alumina coating 3 on the inner surface of the base material 2 and also to cause the dehydrogenating catalyst 4B to be supported on the alumina coating 3 by carrying out the heat treatment step only once.

Alternatively, a pyrolysis tube for manufacturing olefin in accordance with an aspect of the present invention can employ a configuration in which the dehydrogenating catalyst 4B is directly supported on the inner surface of the tubular base material 2 made of the heat resistant metal material, as an example in which the configuration of the pyrolysis tube 1A' illustrated in FIG. 2 and the configuration of the pyrolysis tube 1B illustrated in FIG. 3 are combined.

Types of a pyrolysis tube for manufacturing olefin include, in addition to the type in which a coating is provided on an inner surface of a casting article as in the casting product disclosed in Patent Literature 1, a type in which a protrusion such as a fin is provided on an inner face of the pyrolysis tube for manufacturing olefin in order to stir a fluid and to increase a surface area. The pyrolysis tube for manufacturing olefin in accordance with an embodiment of the present invention can have a configuration in which the dehydrogenating catalyst 4A or the dehydrogenating catalyst 4B is supported on the pyrolysis tube for manufacturing olefin in which the protrusion is provided on the inner face. With the configuration, the pyrolysis tube for manufacturing olefin in accordance with the embodiment of the present invention can heighten a yield of olefin.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

EXAMPLES (i) First Working Example

The following description will discuss Examples of the dehydrogenating catalyst that is used in the pyrolysis tube for manufacturing olefin in accordance with the present invention.

As shown in Table 1 below, in Examples 1 through 6 and Comparative Example 4, dehydrogenating catalysts were used in each of which a metal oxide serving as a catalyst component was supported by powdery $\alpha$-$Al_2O_3$ which was a support for supporting the catalyst component. Moreover, in Comparative Examples 1 through 3, powdery $\alpha$-$Al_2O_3$ was used which was not supporting a dehydrogenating catalyst. By causing $\alpha$-$Al_2O_3$ serving as a support to support the catalyst component, an environment was prepared which was similar to the environments in which the dehydrogenating catalyst (or the catalyst component) is supported on the alumina coating 3 in Embodiment 1 or supported by the carrier 4Bb in Embodiment 2.

Powdery $\alpha$-$Al_2O_3$ which was used in Examples 1 through 6 and Comparative Examples 1 through 4 was JRC-ALO-6 which is a reference catalyst of the Catalysis Society of Japan.

<Method for Manufacturing Dehydrogenating Catalyst>

The following description will discuss methods for manufacturing dehydrogenating catalysts in Examples 1 through 6 and Comparative Example 4.

A dehydrogenating catalyst in Example 1 was manufactured by applying a zinc nitrate ($Zn(NO_3)_2$) aqueous solution to $\alpha$-$Al_2O_3$ serving as a support, and burning them at 700° C. for 3 hours in the atmosphere. In that case, the dehydrogenating catalyst was prepared such that an amount of zinc (Zn) became 5% by weight with respect to a total amount of zinc (Zn) and $\alpha$-$Al_2O_3$. Zinc oxide (ZnO) formed by the burning had a particle size of approximately 20 nm. Hereinafter, the dehydrogenating catalyst obtained by the above method is referred to as "700Zn catalyst".

The dehydrogenating catalyst in Example 2 and Example 3 was manufactured by applying a zinc nitrate ($Zn(NO_3)_2$) aqueous solution to $\alpha$-$Al_2O_3$ serving as a support, and burning them at 850° C. for 3 hours in the atmosphere. In that case, the dehydrogenating catalyst was prepared such that an amount of zinc (Zn) became 5% by weight with respect to a total amount of zinc (Zn) and $\alpha$-$Al_2O_3$. Zinc oxide (ZnO) formed by the burning had a particle size of approximately 30 nm to 50 nm. Hereinafter, the dehydrogenating catalyst obtained by the above method is referred to as "850Zn catalyst".

The dehydrogenating catalyst in Examples 4 through 6 was manufactured by applying a gallium nitrate ($Ga(NO_3)_3$) aqueous solution to $\alpha$-$Al_2O_3$ serving as a support, and burning them at 850° C. for 3 hours in the atmosphere. In that case, the dehydrogenating catalyst was prepared such that an amount of gallium (Ga) became 5% by weight with respect to a total amount of gallium (Ga) and $\alpha$-$Al_2O_3$. Gallium oxide ($Ga_2O_3$) formed by the burning had a particle size of approximately 10 nm to 25 nm. Hereinafter, the dehydrogenating catalyst obtained by the above method is referred to as "850Ga catalyst".

A dehydrogenating catalyst in Comparative Example 4 was manufactured by applying an iron nitrate ($Fe(NO_3)_3$) aqueous solution to $\alpha$-$Al_2O_3$ serving as a support, and burning them at 850° C. for 3 hours in the atmosphere. In that case, the dehydrogenating catalyst was prepared such that an amount of iron (Fe) became 5% by weight with respect to a total amount of iron (Fe) and $\alpha$-$Al_2O_3$. Hereinafter, the dehydrogenating catalyst obtained by the above method is referred to as "850Fe catalyst".

<Ethane Pyrolysis Experiment>

The following description will discuss ethane ($C_2H_6$) pyrolysis experiments which were carried out with use of the 700Zn catalyst, the 850Zn catalyst, the 850Ga catalyst, and the 850Fe catalyst which were obtained with the above described methods and of $\alpha$-$Al_2O_3$.

TABLE 1

| | Catalyst | Burning temperature (° C.) | Reaction temperature (° C.) | Conversion ratio (mol %) | Selectivity (mol %) | Yield (mol %) |
|---|---|---|---|---|---|---|
| Examaple 1 | Zn/$\alpha$-$Al_2O_3$ | 700 | 700 | 1.11 | 84.4 | 0.94 |
| Examaple 2 | Zn/$\alpha$-$Al_2O_3$ | 850 | 750 | 2.53 | 91.4 | 2.31 |
| Examaple 3 | Zn/$\alpha$-$Al_2O_3$ | 850 | 800 | 11.48 | 96.4 | 11.06 |
| Examaple 4 | Ga/$\alpha$-$Al_2O_3$ | 850 | 700 | 1.30 | 93.6 | 1.22 |
| Examaple 5 | Ga/$\alpha$-$Al_2O_3$ | 850 | 750 | 4.36 | 93.2 | 4.06 |
| Examaple 6 | Ga/$\alpha$-$Al_2O_3$ | 850 | 800 | 14.07 | 92.7 | 18.04 |
| Com. Examaple 1 | $\alpha$-$Al_2O_3$ | — | 700 | 0.36 | 91.4 | 0.33 |
| Com. Examaple 2 | $\alpha$-$Al_2O_3$ | — | 750 | 2.25 | 95.1 | 2.14 |
| Com. Examaple 3 | $\alpha$-$Al_2O_3$ | — | 800 | 10.71 | 96.5 | 10.34 |
| Com. Examaple 4 | Fe/$\alpha$-$Al_2O_3$ | 850 | 700 | 1.15 | 61.3 | 0.70 |

Com. Examaple: Comparative Example

In the ethane pyrolysis experiments, first, a quartz tube (having an inner diameter of 4 mm, a length of 180 mm) was filled with a mixture of 100 mg of a sample (700Zn catalyst, 850Zn catalyst, 850Ga catalyst, 850Fe catalyst, or $\alpha$-$Al_2O_3$) and 392 mg of SiC which was an inert solid such that a height of the mixture in the quartz tube became 30 mm. Next, the quartz tube was inserted into a tubular furnace, and a temperature in the quartz tube was raised to an intended reaction temperature (test temperature). Then, a gas was supplied to the quartz tube so as to cause a pyrolysis reaction of ethane in the quartz tube. Flow rates of raw materials were as follows: that is, ethane ($C_2H_6$): 36.2 mL/min, moisture vapor ($H_2O$): 49.4 mL/min, and N2: 196 mL/min. Among the gas flowing out from the quartz tube, hydrogen ($H_2$) and nitrogen ($N_2$) were analyzed with a TCG gas chromatograph (Shimadzu, GC-8A), and ethane ($C_2H_6$), ethylene ($C_2H_4$), carbon monoxide (CO), and methane ($C_2H_4$) are analyzed with an FID gas chromatograph (Shimadzu, GC-8A) provided with a methanizer. Then, as shown in Table 1, a conversion ratio (mol %) of ethane ($C_2H_6$), a selectivity (mol %) of ethylene ($C_2H_4$), and a yield (mol %) of ethylene ($C_2H_4$) were calculated.

In Example 1, the 700Zn catalyst was used, and the reaction temperature was 700° C. In Examples 2 and 3, the 850Zn catalyst was used, and the reaction temperatures were 750° C. and 800° C., respectively. In Examples 4 through 6, the 850Ga catalyst was used, and the reaction temperatures were 700° C., 750° C., and 800° C., respectively. In Comparative Examples 1 through 3, the powdery $\alpha$-$Al_2O_3$ which was not supporting the dehydrogenating catalyst was used, and the reaction temperatures were 700° C., 750° C., and 800° C., respectively. In Comparative Example 4, the 850Fe catalyst was used, and the reaction temperature was 700° C.

Figure 4:
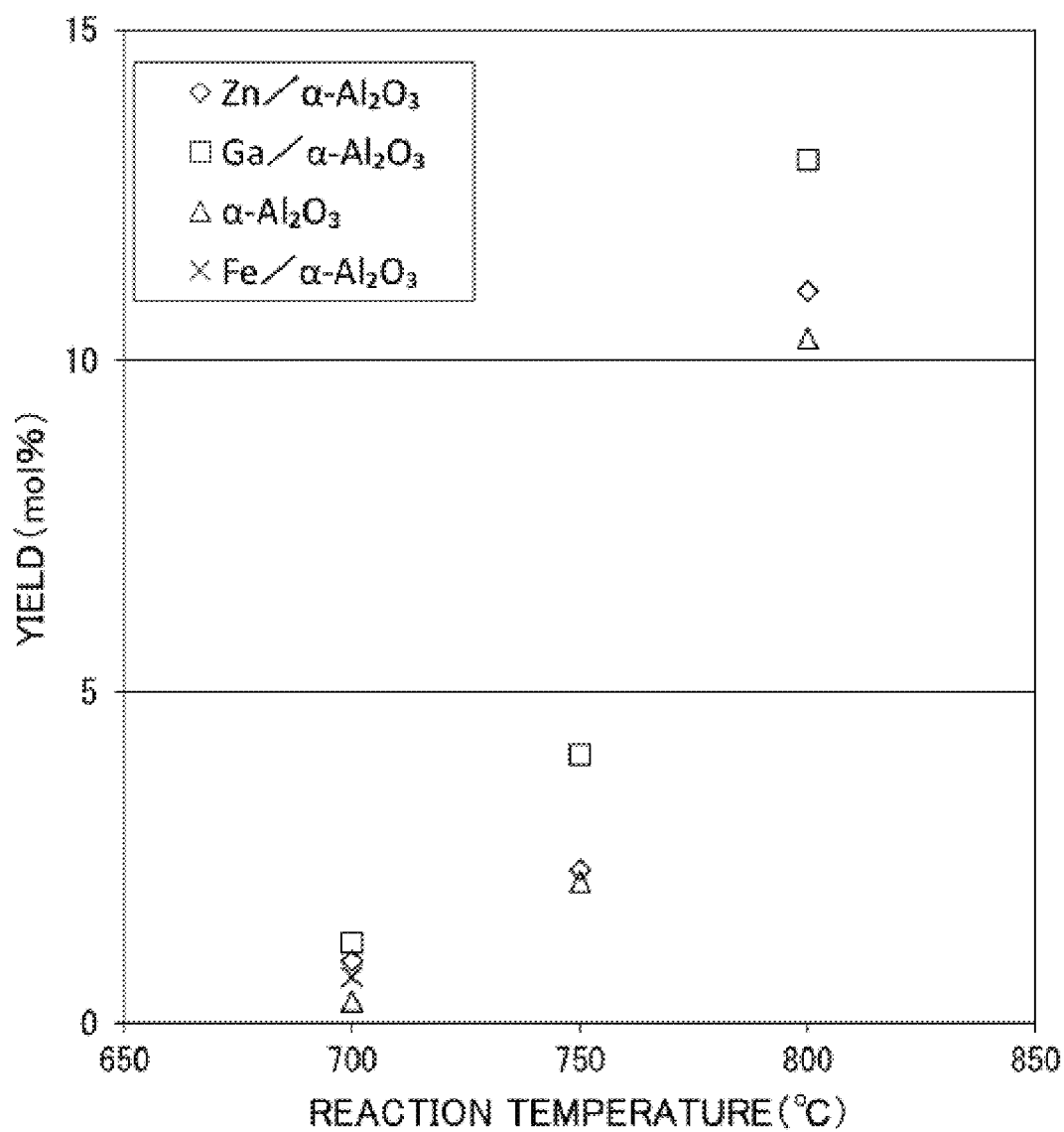
FIG. 4 is a graph showing yields of ethylene with respect to reaction temperatures in Examples and Comparative Examples of the present invention.

Results of the experiments in Examples 1 through 6 and Comparative Examples 1 through 4 are shown in FIG. 4 and Table 1. FIG. 4 is a graph showing yields of ethylene with respect to reaction temperatures in Examples 1 through 6 and Comparative Examples 1 through 4 of the present invention. Note that data shown in FIG. 4 and Table 1 was calculated by analyzing the gas which flew out from the quartz tube 30 minutes after start of reaction.

As shown in FIG. 4 and Table 1, in Examples 1 through 6 in which the dehydrogenating catalyst was used which contained zinc oxide (ZnO) or gallium oxide ($Ga_2O_3$) as a catalyst component, the conversion ratio was higher, the selectivity was substantially equivalent, and the yield was higher, as compared with Comparative Examples 1 through 3 in which the powdery $\alpha$-$Al_2O_3$ which was not supporting a dehydrogenating catalyst was used. That is, it was confirmed that the dehydrogenating catalyst containing zinc oxide (ZnO) or gallium oxide ($Ga_2O_3$) as a catalyst component functioned as a catalyst in the pyrolysis reaction of ethane.

In Comparative Example 4 in which the dehydrogenating catalyst containing iron oxide ($Fe_2O_3$) as a catalyst component was used, the conversion ratio was higher but the selectivity was lower, as compared with Comparative Example 1 in which the powdery $\alpha$-$Al_2O_3$ which was not supporting a dehydrogenating catalyst was used. That is, it was confirmed that the dehydrogenating catalyst containing iron oxide ($Fe_2O_3$) as a catalyst component less functioned as a catalyst in the pyrolysis reaction of ethane.

(ii) Second Working Example

The following description will discuss further Examples of the dehydrogenating catalyst that is used in the pyrolysis tube for manufacturing olefin in accordance with the present invention. Here, Catalyst Examples 1 through 7, which are Examples of the dehydrogenating catalyst, and Comparative Example 5 are described.

The dehydrogenating catalyst in Catalyst Example 1 was manufactured by applying a gallium nitrate ($Ga(NO_3)_3$) aqueous solution to $\alpha$-$Al_2O_3$ serving as a starting material of a carrier for the dehydrogenating catalyst, and burning them at 850° C. for 3 hours in the atmosphere. In that case, the dehydrogenating catalyst was prepared such that an amount of gallium (Ga) became 5% by weight with respect to a total amount of gallium (Ga) and $Al_2O_3$.

The dehydrogenating catalyst of Catalyst Example 2 was manufactured in a manner similar to that of the dehydrogenating catalyst of Catalyst Example 1, except that the burning temperature was 1050° C.

The dehydrogenating catalyst of Catalyst Example 3 was manufactured in a manner similar to that of the dehydrogenating catalyst of Catalyst Example 1, except that the burning temperature was 1300° C.

The dehydrogenating catalyst of Catalyst Example 4 was manufactured in a manner similar to that of the dehydrogenating catalyst of Catalyst Example 1, except that a starting material of a carrier for the dehydrogenating catalyst was $\gamma$-$Al_2O_3$.

The dehydrogenating catalyst of Catalyst Example 5 was manufactured in a manner similar to that of the dehydrogenating catalyst of Catalyst Example 4, except that the burning temperature was 1000° C.

The dehydrogenating catalyst of Catalyst Example 6 was manufactured in a manner similar to that of the dehydrogenating catalyst of Catalyst Example 4, except that the burning temperature was 1050° C.

The dehydrogenating catalyst of Catalyst Example 7 was manufactured in a manner similar to that of the dehydrogenating catalyst of Catalyst Example 4, except that the burning temperature was 1300° C.

In Comparative Example 5, powdery $\alpha$-$Al_2O_3$ (i.e., JRC-ALO-6 which is a reference catalyst of the Catalysis Society of Japan) was used.

<X-Ray Diffraction Analysis>

X-ray diffraction analysis was carried out with respect to the dehydrogenating catalysts in Catalyst Examples 1 through 7.

For the dehydrogenating catalysts in Catalyst Examples 1 through 3 in which $\alpha$-$Al_2O_3$ was used as the starting material of the carrier for the dehydrogenating catalyst, only a diffraction peak of $\alpha$-$Al_2O_3$ was observed (not illustrated). That is, in the dehydrogenating catalysts of Catalyst Examples 1 through 3, gallium oxide was supported by $\alpha$-$Al_2O_3$ which was the starting material.

Figure 5:
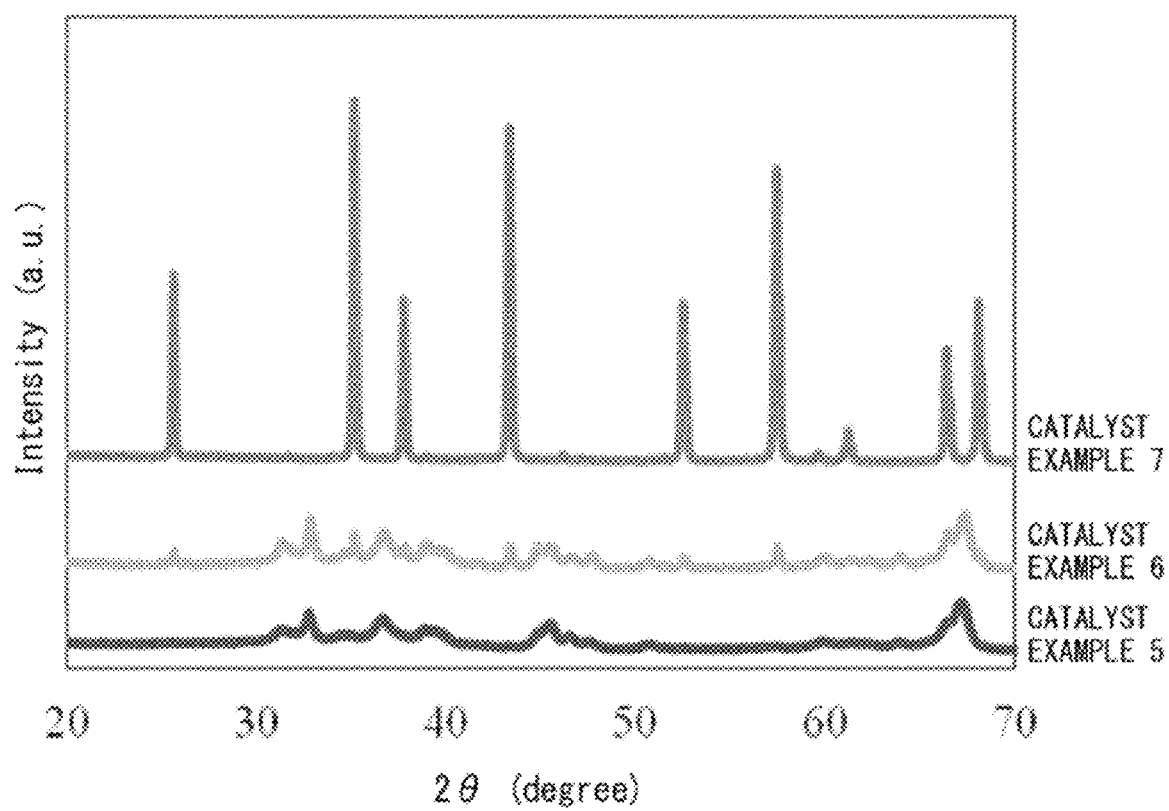
FIG. 5 is a view showing results of X-ray diffraction analysis which was carried out with respect to Catalyst Examples of the dehydrogenating catalyst that is supported on the pyrolysis tube for manufacturing olefin in accordance with an aspect of the present invention.

Among the dehydrogenating catalysts in Catalyst Examples 4 through 8 in which $\gamma$-$Al_2O_3$ was used as the starting material of the carrier for the dehydrogenating catalyst, for the dehydrogenating catalyst of Catalyst Example 4 subjected to the heat treatment of 850° C., a diffraction peak of $\gamma$-$Al_2O_3$ was observed (not illustrated). That is, in the dehydrogenating catalyst of Catalyst Example 4, gallium oxide was supported by $\gamma$-$Al_2O_3$ which was the starting material. Results of X-ray diffraction analysis carried out with respect to the dehydrogenating catalysts in Catalyst Examples 5 through 7 are shown in FIG. 5. As shown in FIG. 5, for the dehydrogenating catalyst of Catalyst Example 5 subjected to the heat treatment of 1000° C. and the dehydrogenating catalyst of Catalyst Example 6 subjected to the heat treatment of 1050° C., a diffraction peak of $\theta$-$Al_2O_3$ was mainly observed. That is, in the dehydrogenating catalysts of Catalyst Examples 5 and 6, gallium oxide (or a part of gallium oxide) was supported by the carrier which was mainly constituted by $\theta$-$Al_2O_3$. Note that, in the dehydrogenating catalyst of Catalyst Example 6, a diffraction peak of $\alpha$-$Al_2O_3$ was concurrently observed, in addition to the diffraction peak of $\theta$-$Al_2O_3$. As shown in FIG. 5, for the dehydrogenating catalyst of Catalyst Example 7 subjected to the heat treatment of 1300° C., a diffraction peak of $\alpha$-$Al_2O_3$ was mainly observed. That is, in the dehydrogenating catalyst of Catalyst Example 7, gallium oxide was supported by the carrier which was mainly constituted by $\alpha$-$Al_2O_3$.

<Ethane Pyrolysis Experiment>

Figure 6:
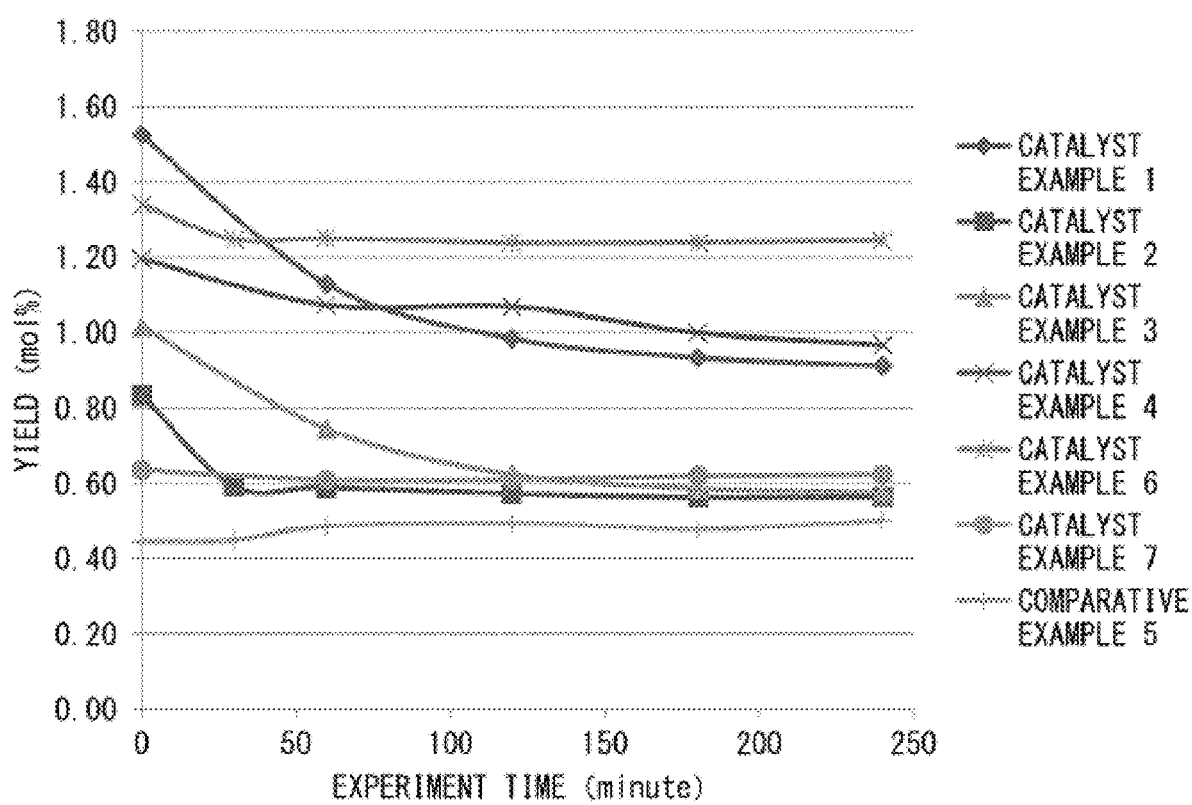
FIG. 6 is a graph showing change of yield of ethylene over time in ethane pyrolysis experiments carried out with use of the dehydrogenating catalyst that is supported on the pyrolysis tube for manufacturing olefin of an aspect of the present invention and of powdery α-$Al_2O_3$ of Comparative Example.

The following description will discuss ethane ($C_2H_6$) pyrolysis experiments which were carried out with use of the dehydrogenating catalysts of Catalyst Examples 1 through 4, 6, and 7 and of powdery $\alpha\text{-}Al_2O_3$ of Comparative Example 5, with reference to FIG. 6. Note that methods for carrying out the pyrolysis experiments are similar to those of the ethane pyrolysis experiments in First Working Example, and are therefore not repeatedly described here.

FIG. 6 is a graph showing change of yield of ethylene over time in ethane pyrolysis experiments carried out with use of the dehydrogenating catalysts of Catalyst Examples 1 through 4, 6, and 7 and of powdery $\alpha\text{-}Al_2O_3$ of Comparative Example 5. As shown in FIG. 6, the dehydrogenating catalysts of Catalyst Examples 1 through 4, 6, and 7 achieved the yields of ethylene which were higher than that achieved by the powdery $\alpha\text{-}Al_2O_3$ of Comparative Example 5.

Moreover, with the dehydrogenating catalysts of Catalyst Examples 1 through 3 in which $\alpha\text{-}Al_2O_3$ was used as the starting material of the carrier for the dehydrogenating catalyst, the yield of ethylene greatly decreased as the experiment time became longer. On the other hand, with the dehydrogenating catalysts of Catalyst Examples 4, 6, and 7 in which $\gamma\text{-}Al_2O_3$ was used as the starting material of the carrier for the dehydrogenating catalyst, the yield of ethylene did not decrease (or not greatly decrease) even when the experiment time became longer. In particular, with the dehydrogenating catalyst of Catalyst Example 4 subjected to the heat treatment of 850° C. and with the dehydrogenating catalyst of Catalyst Example 6 subjected to the heat treatment of 1050° C., the yields of ethylene were higher than those achieved with the other dehydrogenating catalysts.

<Measurement of Specific Surface Area>

Next, BET specific surface area measurement was carried out with respect to the dehydrogenating catalysts of Catalyst Examples 2, 3, and 6. Results of the measurement are shown in Table 2.

TABLE 2

| | Catalyst Examaple 2 | Catalyst Examaple 3 | Catalyst Examaple 6 |
|---|---|---|---|
| Specific surface area ($m^2/g$) | 5.5 | 4.4 | 49.3 |

As shown in Table 2, the dehydrogenating catalyst of Catalyst Example 6 was approximately 10 times larger in specific surface area than the dehydrogenating catalysts of Catalyst Examples 2 and 3. This is because, in the dehydrogenating catalysts of Catalyst Examples 2 and 3, $Al_2O_3$ serving as the carrier is mainly $\alpha\text{-}Al_2O_3$ whose specific surface area is smaller, whereas, in the dehydrogenating catalyst of Catalyst Example 6, $Al_2O_3$ serving as the carrier is mainly $\theta\text{-}Al_2O_3$ whose specific surface area is larger.

<Measurement of TEM-EDS>

The following description will discuss results of observation and measurement carried out with respect to the dehydrogenating catalysts of Catalyst Examples 2 and 6 by using transmission electron microscope-energy dispersive spectroscopy (TEM-EDS) with reference to FIG. 7. FIG. 7 is a view showing results of observation and measurement with respect to the dehydrogenating catalysts of Catalyst Examples 2 and 6 by using transmission electron microscope-energy dispersive spectroscopy (TEM-EDS). Specifically, FIG. 7 shows high-angle annular dark field (HAADF) images and results of EDS mapping measurement carried out with respect to Al and Ga. As shown in FIG. 6, in Catalyst Example 2 in which $\alpha\text{-}Al_2O_3$ was used, gallium oxide was aggregated on $Al_2O_3$ serving as a carrier. On the other hand, in Catalyst Example 6 in which $\gamma\text{-}Al_2O_3$ was used, gallium oxide was dispersed on $Al_2O_3$ serving as a carrier (i.e., a composite oxide was formed). This result conforms to the result of the above described ethane pyrolysis experiment. This seems to be because, in Catalyst Example 6 in which $\gamma\text{-}Al_2O_3$ was used, gallium oxide was dispersed on $Al_2O_3$, and therefore aggregation of gallium oxide in the ethane decomposition experiment was inhibited.

[Recap]

The pyrolysis tube for manufacturing olefin in accordance with an aspect of the present invention is configured to include: a tubular base material made of a heat resistant metal material; and a dehydrogenating catalyst which is supported on an inner surface of the tubular base material.

According to the configuration, the dehydrogenating catalyst can function as a dehydrogenating catalyst in a pyrolysis reaction of a hydrocarbon raw material. As a result, in pyrolysis carried out with use of the pyrolysis tube, it is possible to facilitate a dehydrogenation reaction of a hydrocarbon raw material such as ethane or naphtha, and this makes it possible to improve a yield of olefin to be generated.

The pyrolysis tube for manufacturing olefin in accordance with an aspect of the present invention is configured to include: a tubular base material made of a heat resistant metal material; a metal oxide coating which is provided on an inner surface of the tubular base material; and a dehydrogenating catalyst which is supported on a surface of the metal oxide coating.

According to the configuration, the metal oxide coating is provided on the inner surface of the base material, and therefore the metal oxide coating, which serves as a barrier, prevents oxygen, carbon, nitrogen, and the like from intruding inside the base material. Further, the dehydrogenating catalyst is supported on the surface of the metal oxide coating. From this, the dehydrogenating catalyst can function as a catalyst in a pyrolysis reaction of a hydrocarbon raw material. As a result, in pyrolysis carried out with use of the pyrolysis tube, it is possible to facilitate a dehydrogenation reaction of a hydrocarbon raw material such as ethane or naphtha, and this makes it possible to improve a yield of olefin to be generated.

Moreover, nickel (Ni) and the like contained in the base material have a function to facilitate formation of coke and, by providing the metal oxide coating, it is possible to prevent the hydrocarbon raw material and the heat resistant metal material from making direct contact with each other.

In the pyrolysis tube in accordance with an aspect of the present invention, it is preferable that the metal oxide coating is made of at least one selected from the group consisting of $Al_2O_3$, $Cr_2O_3$, and $MnCr_2O_4$. Note that those metal oxides have a barrier function and can support the dehydrogenating catalyst.

According to the configuration, it is possible to prevent intrusion of oxygen, carbon, nitrogen, and the like, and also to cause the dehydrogenating catalyst to be supported on the surface of the pyrolysis tube.

In the pyrolysis tube in accordance with an aspect of the present invention, it is preferable that the dehydrogenating catalyst contains, as a catalyst component, at least one selected from the group consisting of oxides of metallic elements in the group 2B of the periodic table, oxides of metallic elements in the group 3B of the periodic table, and oxides of metallic elements in the group 4B of the periodic table.

According to the configuration, the oxides of metallic elements in the group 2B of the periodic table, the oxides of metallic elements in the group 3B of the periodic table, and the oxides of metallic elements in the group 4B of the periodic table are acidic oxides each of which functions as a catalyst for facilitating a dehydrogenation reaction of a hydrocarbon raw material such as ethane or naphtha. As a result, in pyrolysis carried out with use of the pyrolysis tube, it is possible to improve a yield of olefin to be generated.

In the pyrolysis tube in accordance with an aspect of the present invention, it is preferable that the dehydrogenating catalyst contains, as a catalyst component, at least one selected from the group consisting of Zn oxide, Ga oxide, Sn oxide, Ge oxide, and In oxide.

According to the configuration, the Zn oxide, the Ga oxide, the Sn oxide, the Ge oxide, and the In oxide are acidic oxides each of which functions as a catalyst for facilitating a dehydrogenation reaction of a hydrocarbon raw material such as ethane or naphtha. As a result, in pyrolysis carried out with use of the pyrolysis tube, it is possible to improve a yield of olefin to be generated.

In the pyrolysis tube in accordance with an aspect of the present invention, the dehydrogenating catalyst can contain the catalyst component and a carrier which supports the catalyst component. Note that the carrier is preferably $Al_2O_3$.

According to the configuration, the dehydrogenating catalyst, which contains the catalyst component and the carrier supporting the catalyst component, are supported on the base material or on the surface of the metal oxide coating. With the configuration, it is possible to enlarge a surface area, in which the catalyst component can make contact with the hydrocarbon raw material, by the carrier. As a result, dehydrogenation reaction locations of hydrocarbon can be increased in addition to the pyrolysis reaction of hydrocarbon, and this makes it possible to improve a yield of olefin obtained from the hydrocarbon raw material such as ethane or naphtha.

In the pyrolysis tube in accordance with an aspect of the present invention, it is preferable that a specific surface area of $Al_2O_3$ serving as the carrier is 20 $m^2$/g or more.

According to the configuration, it is possible to highly disperse the catalyst component in the carrier. As a result, it is possible to improve a yield of olefin in a pyrolysis reaction by which a hydrocarbon raw material is pyrolyzed into olefin.

In the pyrolysis tube in accordance with an aspect of the present invention, it is preferable that the catalyst component is Ga oxide, and $Al_2O_3$ serving as the carrier is at least partially $\theta$-$Al_2O_3$.

According to the configuration, Ga oxide and $\theta$-$Al_2O_3$ form a composite oxide, and this makes it possible to inhibit aggregation of the catalyst component 4Ba in the pyrolysis reaction for pyrolyzing the hydrocarbon raw material into olefin. Consequently, it is possible to maintain a state in which a yield of olefin is high for a long time, and this makes it possible to further improve the yield of olefin.

The method for manufacturing a dehydrogenating catalyst in accordance with an aspect of the present invention is a method for manufacturing a dehydrogenating catalyst which is to be supported on the pyrolysis tube for manufacturing olefin, the method including the steps of: (a) causing a metal salt aqueous solution to adhere to $\gamma$-$Al_2O_3$, the metal salt aqueous solution containing at least one metallic element selected from the group consisting of metallic elements in the group 2B of the periodic table, metallic elements in the group 3B of the periodic table, and metallic elements in the group 4B of the periodic table; and (b) subjecting the $\gamma$-$Al_2O_3$, to which the metal salt aqueous solution has adhered in the step (a), to heat treatment at a temperature of 1100° C. or lower.

According to the configuration, heat treatment at the temperature of 1100° C. or lower is carried out with respect to $\gamma$-$Al_2O_3$ to which the metal salt aqueous solution has adhered, and this makes it possible to inhibit $\gamma$-$Al_2O_3$ from being completely phase-transformed in the step (b) into $\alpha$-$Al_2O_3$ having a smaller specific surface area. From this, it is possible to inhibit decrease in specific surface area of $Al_2O_3$ serving as the carrier. As a result, it is possible to highly disperse the catalyst component in $Al_2O_3$ serving as the carrier.

In the method in accordance with an aspect of the present invention for manufacturing the dehydrogenating catalyst, it is preferable that the temperature of the heat treatment in the step (b) falls within a range from 1000° C. to 1100° C.

According to the configuration, although a specific mechanism is not clear, it seems that at least part of $\gamma$-$Al_2O_3$ is phase-transformed into $\theta$-$Al_2O_3$ during heat treatment, $\theta$-$Al_2O_3$ and at least part of $Al_2O_3$ are coupled with the catalyst component in the phase transformation, and thus a composite oxide is formed. From this, it is possible to inhibit aggregation of the catalyst component in the pyrolysis reaction for pyrolyzing the hydrocarbon raw material into olefin.

INDUSTRIAL APPLICABILITY

The present invention is applicable to a pyrolysis tube for pyrolyzing a hydrocarbon raw material such as ethane or naphtha into olefin.

REFERENCE SIGNS LIST 1A, 1A', 1B: Pyrolysis tube for manufacturing olefin
2: Base material
3: Alumina coating (metal oxide coating)
4A, 4B: Dehydrogenating catalyst
4Ba: Catalyst component
4Bb: Carrier

What is claimed:
1. A pyrolysis tube for manufacturing olefin, said pyrolysis tube comprising:
 a tubular base material made of a heat resistant metal material; and
 a dehydrogenating catalyst which is supported on an inner surface of the tubular base material;
  wherein the dehydrogenating catalyst contains a catalyst component and a carrier which supports the catalyst component;
   wherein the carrier is $Al_2O_3$ and wherein a specific surface area of $Al_2O_3$ serving as the carrier is 20 $m^2$/g or more; and
  wherein the catalyst component and the carrier form a composite oxide or a solid solution.
2. A pyrolysis tube for manufacturing olefin, said pyrolysis tube comprising:
 a tubular base material made of a heat resistant metal material;
 a metal oxide coating which is provided on an inner surface of the tubular base material; and a dehydrogenating catalyst which is supported on a surface of the metal oxide coating;
wherein the dehydrogenating catalyst contains a catalyst component and a carrier which supports the catalyst component;
wherein the carrier is $Al_2O_3$ and wherein a specific surface area of $Al_2O_3$ serving as the carrier is 20 $m^2/g$ or more; and
wherein the catalyst component and the carrier form a composite oxide or a solid solution.

3. The pyrolysis tube as set forth in claim 2, wherein the metal oxide coating is made of at least one selected from the group consisting of $Al_2O_3$, $Cr_2O_3$, and $MnCr_2O_4$.

4. The pyrolysis tube as set forth in claim 1, wherein the dehydrogenating catalyst contains, as a catalyst component, at least one selected from the group consisting of oxides of metallic elements in the group 2B of the periodic table, oxides of metallic elements in the group 3B of the periodic table, and oxides of metallic elements in the group 4B of the periodic table.

5. The pyrolysis tube as set forth in claim 1, wherein the dehydrogenating catalyst contains, as a catalyst component, at least one selected from the group consisting of Zn oxide, Ga oxide, Sn oxide, Ge oxide, and In oxide.

6. A pyrolysis tube for manufacturing olefin, said pyrolysis tube comprising:
a tubular base material made of a heat resistant metal material; and
a dehydrogenating catalyst which is supported on an inner surface of the tubular base material;
wherein the dehydrogenating catalyst contains a catalyst component and a carrier which supports the catalyst component;
wherein the catalyst component is Ga oxide, the carrier is $Al_2O_3$, and $Al_2O_3$ serving as the carrier is at least partially $\theta$-$Al_2O_3$; and
wherein the catalyst component and the carrier form a composite oxide or a solid solution.

7. A method for manufacturing a pyrolysis tube for manufacturing olefin recited in claim 1, said method comprising the step of:
(a) preparing a dehydrogenating catalyst which is to be supported on a pyrolysis tube, the step (a) including:
(b) causing a metal salt aqueous solution to adhere to $\gamma$-$Al_2O_3$, the metal salt aqueous solution containing at least one metallic element selected from the group consisting of metallic elements in the group 2B of the periodic table, metallic elements in the group 3B of the periodic table, and metallic elements in the group 4B of the periodic table; and
(c) subjecting the $\gamma$-$Al_2O_3$, to which the metal salt aqueous solution has adhered in the step (a), to heat treatment at a temperature of 1100° C. or lower.

8. The method as set forth in claim 7, wherein the temperature of the heat treatment in the step (c) falls within a range from 1000° C. to 1100° C.

* * * * *